US010209249B2

(12) United States Patent
Aizawa et al.

(10) Patent No.: US 10,209,249 B2
(45) Date of Patent: Feb. 19, 2019

(54) LABELLED SILICA NANOPARTICLES FOR IMMUNOCHROMATOGRAPHIC REAGENT, IMMUNOCHROMATOGRAPHIC TEST STRIP USING THE SAME, AND IMMUNOCHROMOMATOGRAPHIC FLUORESCENCE-DETECTING SYSTEM OR RADIATION-DETECTING SYSTEM

(71) Applicant: THE FURUKAWA ELECTRIC CO., LTD., Tokyo (JP)

(72) Inventors: Hideki Aizawa, Tokyo (JP); Michio Ohkubo, Tokyo (JP)

(73) Assignee: THE FURUKAWA ELECTRIC CO., LTD., Tokyo (JP)

( * ) Notice: Subject to any disclaimer, the term of this patent is extended or adjusted under 35 U.S.C. 154(b) by 133 days.

(21) Appl. No.: 14/942,218

(22) Filed: Nov. 16, 2015

(65) Prior Publication Data
US 2016/0069875 A1 Mar. 10, 2016

Related U.S. Application Data

(62) Division of application No. 13/095,196, filed on Apr. 27, 2011, now abandoned, which is a division of
(Continued)

(30) Foreign Application Priority Data

Jun. 8, 2007 (JP) ................................. 2007-153366

(51) Int. Cl.
*G01N 33/558* (2006.01)
*G01N 33/543* (2006.01)
(Continued)

(52) U.S. Cl.
CPC ........ *G01N 33/54366* (2013.01); *B82Y 15/00* (2013.01); *G01N 21/6428* (2013.01);
(Continued)

(58) Field of Classification Search
None
See application file for complete search history.

(56) References Cited

U.S. PATENT DOCUMENTS 3,975,511 A * 8/1976 Vann ...................... A61K 39/44
250/303
6,254,852 B1 * 7/2001 Glajch ................. A61K 49/225
424/9.52
(Continued)

FOREIGN PATENT DOCUMENTS

JP 2002-303629 A 10/2002
JP 2003-262638 A 9/2003
(Continued)

OTHER PUBLICATIONS

Wang et al, "Watching Silica Nanoparticles Glow in the Biological World", Analytical Chemistry, 78.3: 646-654, Feb. 1, 2006.*
(Continued)

*Primary Examiner* — Christopher L Chin
(74) *Attorney, Agent, or Firm* — Birch, Stewart, Kolasch & Birch, LLP

(57) ABSTRACT

Labelled silica nanoparticles for immunochromatographic reagent, comprising silica nanoparticles containing a labelled substance.

10 Claims, 2 Drawing Sheets

Related U.S. Application Data application No. 12/155,622, filed on Jun. 6, 2008, now Pat. No. 7,955,866.

(51) Int. Cl.
| | |
|---|---|
| *B82Y 15/00* | (2011.01) |
| *G01N 21/64* | (2006.01) |
| *G01N 33/58* | (2006.01) |
| *G01N 21/77* | (2006.01) |
| *G01N 33/552* | (2006.01) |

(52) U.S. Cl.
CPC ....... *G01N 21/77* (2013.01); *G01N 33/54346* (2013.01); *G01N 33/54353* (2013.01); *G01N 33/552* (2013.01); *G01N 33/587* (2013.01); *G01N 2021/7753* (2013.01); *G01N 2021/7759* (2013.01); *Y10S 977/70* (2013.01); *Y10S 977/773* (2013.01); *Y10S 977/788* (2013.01); *Y10S 977/918* (2013.01); *Y10T 428/2982* (2015.01)

(56) References Cited

U.S. PATENT DOCUMENTS

| | | | |
|---|---|---|---|
| 6,528,325 B1 * | 3/2003 | Hubscher | G01N 33/558 |
| | | | 422/400 |
| 7,141,431 B2 | 11/2006 | Chandler et al. | |
| 2006/0008924 A1 * | 1/2006 | Anker | G01N 33/587 |
| | | | 436/526 |

FOREIGN PATENT DOCUMENTS

| | | | | |
|---|---|---|---|---|
| JP | 2005-214670 A | 8/2005 | | |
| JP | 2006-67979 A | 3/2006 | | |
| JP | 2006-194785 A | 7/2008 | | |
| WO | WO 03/003015 A2 | 1/2003 | | |
| WO | WO 2006/070582 A1 | 7/2006 | | |
| WO | WO 2006073500 A2 * | 7/2006 | ............... | B82Y 5/00 |
| WO | WO 2007/007849 A1 | 1/2007 | | |

OTHER PUBLICATIONS

Brandriss et al, "Radiolabeled Se-silica nanoparticles: synthesis, characterization and coating with functionalzed alkylsilane compounds", Reactive Polymers, 25, 1995, 111-125.*
Decision to Grant dated Jul. 28, 2009, in corresponding Japanese Application No. 2007-153366.
Ow et al., "Bright and Stable Core-Shell Fluorescent Silica Nanoparticles", Nano Letters, vol. 5, No. 1, pp. 113-117, 2005.
Advisory Action dated Jul. 28, 2014, issued in U.S. Appl. No. 13/095,196.
Final Office Action dated Mar. 14, 2014, issued in U.S. Appl. No. 13/095,196.
Non-Final Office Action dated Nov. 15, 2013, issued in U.S. Appl. No. 13/095,196.
Non-Final Office Action dated Sep. 6, 2013, issued in U.S. Appl. No. 13/095,196.
Non-Final Office Action dated Sep. 7, 2010, issued in U.S. Appl. No. 12/155,622.
Notice of Allowability dated Jan. 31, 2011, issued in U.S. Appl. No. 12/155,622.
Office Action dated Jun. 23, 2010, issued in U.S. Appl. No. 12/155,622.

* cited by examiner

LABELLED SILICA NANOPARTICLES FOR IMMUNOCHROMATOGRAPHIC REAGENT, IMMUNOCHROMATOGRAPHIC TEST STRIP USING THE SAME, AND IMMUNOCHROMOMATOGRAPHIC FLUORESCENCE-DETECTING SYSTEM OR RADIATION-DETECTING SYSTEM

CROSS REFERENCE

This application is a Divisional of co-pending application Ser. No. 13/095,196 filed on Apr. 27, 2011, which is a Divisional of Ser. No. 12/155,622 filed Jun. 6, 2008 (now U.S. Pat. No. 7,955,866), the entire contents of which are hereby incorporated by reference, and to which priority is claimed under 35 U.S.C. § 120. Priority is also claimed, under 35 U.S.C. § 119, to Japanese Application No. 2007-153366 filed Jun. 8, 2007, the entire contents of which are hereby incorporated by reference.

FIELD

The present invention relates to silica nanoparticles containing a labelled substance and an immunochromatographic reagent allowing simultaneous multi-item detection by using the same. The present invention also relates to an immunochromatographic test strip using the immunochromatographic reagent, and an immunochromatographic fluorescence-detecting system employing a fluorescent substance or a radioactive substance as the labelled substance or a radiation-detecting system employing a radioactive substance as the labelled substance that allows high-sensitivity detection.

BACKGROUND

The immunochromatographic method is an immunological test method of determining the presence or absence of an analyte substance by making the analyte substance captured by labelled particles move through a porous support in capillary phenomenon, efficiently bringing the labelled particles into contact with a capturing substance locally (e.g., linearly) immobilized on the porous support and thus, concentrating the analyte substance, and making the immobilized line colored by the capturing substance. The immunochromatographic method has the following three characteristics:

(1) Rapid test is possible, as the period needed for test is 20 minutes or less.

(2) Multi-item analysis is possible, because the operation was simple and easy, demanding only dropwise application of the sample.

(3) No special detector is needed and the test is simple and easy, allowing test by general users.

Because of these characteristics, the immunochromatographic method has been applied as a pregnancy test reagent and an influenza test reagent, and attracting attention as a new POCT (Point Of Care Testing) method.

The POCT is a test for diagnosis that is carried out at a place as close to the patient as possible. Conventionally, samples collected such as blood, urine and infected organs were sent to the central laboratory of hospital or a professional laboratory for analysis for data, and thus, a long period (e.g., at least one day) was needed before final diagnosis. The POCT above promises rapid and accurate therapy, based on test information obtained instantaneously and allows emergency tests in hospital and during operation, and thus, there is an increased need for it recently in the medical settings.

Currently, gold nanoparticles are used most frequently as the labelled substance in the immunochromatographic method. The gold nanoparticles have a large absorbance and are thus superior in visibility, but have only a single color, consequently causing a problem of restriction of the color for use. In addition, gold particles having a larger particle diameter often aggregate and blacken over time, causing a problem that it was difficult to make the gold particles develop a clear color.

SUMMARY

The present invention resides in labelled silica nanoparticles for an immunochromatographic reagent, comprising silica nanoparticles containing a labelled substance.

Further, the present invention resides in an immunochromatographic reagent, comprising the labelled silica nanoparticles.

Further, the present invention resides in an immunochromatographic test strip, comprising a sample application member, a member impregnated with the labelled silica nanoparticles as the immunochromatographic reagent, a membrane having an antibody-immobilized region, and an absorption pad that are connected in series.

Further, the present invention resides in an immunochromatographic fluorescence-detecting system, comprising the immunochromatographic reagent, wherein the wavelength of an excitation light source used for detection of the fluorescence emitted from the silica nanoparticles is 200 nm to 600 nm.

Further, the present invention resides in an immunochromatographic radiation-detecting system, comprising the immunochromatographic reagent, wherein radiation emitted from the silica nanoparticles is measured with a Geiger counter or by photosensitizing an X-ray film.

Other and further features and advantages of the invention will appear more fully from the following description, with taken in connection with the accompanying drawings.

BRIEF DESCRIPTION OF THE DRAWINGS

FIG. 1b is a cross-sectional view of the immunochromatographic test strip in the top view shown in FIG. 1a.

DETAILED DESCRIPTION

Figure 1A:
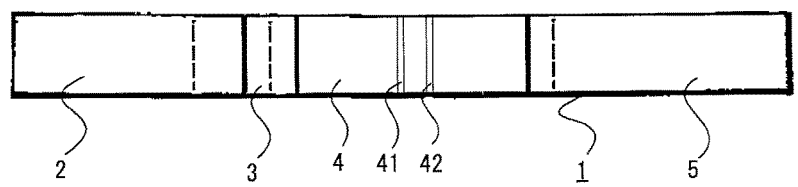
FIG. 1a is a top view illustrating an immunochromatographic test strip of the present invention.

According to the present invention, there is provided the following means.

(1) Labelled silica nanoparticles for an immunochromatographic reagent, comprising silica nanoparticles containing a labelled substance.

(2) The labelled silica nanoparticles for an immunochromatographic reagent according to the item (1), wherein the labelled substance is a fluorescent substance or a light-absorbing substance.

(3) The labelled silica nanoparticles for an immunochromatographic reagent according to the item (1), wherein the labelled substance is a radioactive substance.

(4) The labelled silica nanoparticles for an immunochromatographic reagent according to any one of the items (1) to (3), wherein the average diameter of the labelled silica nanoparticles is 20 to 1000 nm.

(5) The labelled silica nanoparticles for an immunochromatographic reagent according to any one of the items (1) to (4), wherein the nanoparticles contain no surfactant.

(6) The labelled silica nanoparticles for an immunochromatographic reagent according to any one of the items (1) to (5), wherein the nanoparticles are surface-modified with an analyte-recognizing substance.

(7) The labelled silica nanoparticles for an immunochromatographic reagent according to the item (6), wherein the analyte-recognizing substance is an antibody.

(8) The labelled silica nanoparticles for an immunochromatographic reagent according to the item (7), wherein the antibody binding amount to a surface area of 1 $m^2$ of the silica nanoparticles is 0.35 mg to 7 mg.

(9) An immunochromatographic reagent, comprising the labelled silica nanoparticles according to any one of the items (6) to (8).

(10) The immunochromatographic reagent according to the item (9), wherein two or more kinds of analytes are detected simultaneously by using two or more kinds of labelled silica nanoparticles distinguished from each other by difference in the kind and the content of the labelled substance.

(11) The immunochromatographic reagent according to the item (9) or (10), wherein the labelled substance is a light-absorbing substance that has a maximum absorption wavelength in the absorption spectrum thereof in the range of 200 to 800 nm.

(12) The immunochromatographic reagent according to the item (11), wherein the molar extinction coefficient of the silica nanoparticles at the maximum wavelength in the absorption spectrum is $5\times10^7 M^{-1} cm^{-1}$ or more.

(13) The immunochromatographic reagent according to the item (9) or (10), wherein the labelled substance is a fluorescent substance and the reagent allows high-sensitivity detection by detection of fluorescence emitted from the silica nanoparticles containing the fluorescent substance.

(14) The immunochromatographic reagent according to the item (13), wherein the fluorescence is blue fluorescence, yellow fluorescence, orange fluorescence or red fluorescence.

(15) An immunochromatographic test strip, comprising a sample application member, a member impregnated with the labelled silica nanoparticles as the immunochromatographic reagent according to any one of the items (9) to (14), a membrane having an antibody-immobilized region, and an absorption pad that are connected in series.

(16) The immunochromatographic test strip according to the item (15), wherein two or more kinds of analytes are detected simultaneously, based on the difference in hue of color formation or fluorescence wavelength in a single antibody-immobilized region.

(17) An immunochromatographic fluorescence-detecting system, comprising the immunochromatographic reagent according to the item (13) or (14), wherein the wavelength of an excitation light source used for detection of the fluorescence emitted from the silica nanoparticles is 200 nm to 600 nm.

(18) The immunochromatographic fluorescence-detecting system according to the item (17), further comprising a filter transmitting the excitation light at a particular wavelength from the excitation light source and a filter eliminating the excitation light and transmitting only the fluorescence.

(19) The immunochromatographic fluorescence-detecting system according to the item (18), further comprising a photoelectron multiplier or a CCD detector detecting the fluorescence, wherein the system allows quantitative determination of the analyte by detection of the fluorescence and measurement of the fluorescent intensity with the photoelectron multiplier or the CCD detector.

(20) The immunochromatographic fluorescence-detecting system according to any one of the items (17) to (19), wherein the excitation light source is a mercury lamp, a halogen lamp, or a xenon lamp.

(21) The immunochromatographic radiation-detecting system, comprising the immunochromatographic reagent according to the item (9), wherein radiation emitted from the silica nanoparticles is measured with a Geiger counter or by photosensitizing an X-ray film.

First, the labelled silica nanoparticles for an immunochromatographic reagent of the present invention will be described.

The labelled silica nanoparticles for an immunochromatographic reagent of the present invention comprise silica nanoparticles containing a labelled substance.

In the present invention, the "silica nanoparticles" mean colloidal silica particles having an average diameter of 1,000 nm or less.

Generally, silica refers to a three-dimensional structure consisting of silicon and oxygen atoms forming siloxane bonds (Si—O bonds) with each other, but in the present invention, it also includes three-dimensional structures of silicon and oxygen atoms containing organosiloxane components.

In the present invention, the average diameter of the labelled silica nanoparticles is preferably 20 to 1000 nm, more preferably 20 to 600 nm, furthermore preferably 60 to 300 nm. An excessively smaller particle diameter leads to deterioration in detection sensitivity, while an excessively large particle diameter may cause clogging of the porous support (membrane) used in the immunochromatographic method.

In the present invention, the average diameter is an average diameter of the circle (average circle-equivalent diameter) obtained by measuring the total projected area of 50 randomly-selected silica nanoparticles in an image obtained under transmission electron microscope (TEM), scanning electron microscope (SEM) or the like using an image processing equipment, dividing the total area with the number of the silica particles (50), and determining the circle having an area equivalent to that.

The variation coefficient, so-called CV value, of the particle size distribution is not particularly limited, but preferably 10% or less, more preferably 8% or less.

In the present description and the claims thereof, a term "monodispersion" is used for particles having a CV value of 15% or less.

In the present invention, the silica particle to be used is not particularly limited, and silica particles produced by any preparation method may be used. Examples thereof include the silica particles prepared by the sol-gel process, for example as described in Journal of Colloid and Interface Science, 159, 150-157 (1993).

It is particularly preferred that silica nanoparticles containing the labelled substance prepared according to a method of preparing colloidal silica particles containing a fluorescent dye compound described in WO2007/074722A1 are used.

Specifically, the silica nanoparticles containing the labelled substance can be prepared by:

(a) obtaining a product by reacting the labelled substance with a silane-coupling agent to form a chemical bond, such as a covalent bond, an ionic bond or the like, or to adsorb the labelled substance onto the silane-coupling agent, and (b) polymerizing one or more silane compounds to the product.

As the preferred embodiment of the method of preparing silica nanoparticles containing the labelled substance, the silica nanoparticles containing the labelled substance can be prepared by:

(a) obtaining a product by allowing the labelled substance having an active group such as N-hydroxysuccinimide (NHS) ester group, a maleimide group, an isocyanate group, an isothiocyanate group, an aldehyde group, a para-nitrophenyl group, a diethoxymethyl group, an epoxy group, or a cyano group, to react with a silane-coupling agent having a substituent group (such as amino group, hydroxyl group, or thiol group) reactive with the active group, to form a covalent bond, and (b) polymerizing one or more silane compounds to the product.

Specific examples of the active group-containing the labelled substances include NHS ester group-containing labelled substances such as 5- (and 6)-carboxytetramethylrhodamine succinimidyl ester (trade name, manufactured by emp Biotech GmbH).

Specific examples of the radioactive substances having such an active group include NHS ester derivatives of carboxyl group-containing radioactive substances, such as Phenylacetic acid, [acetate-1,2-14C] (product name, manufactured by Daiichi Pure Chemicals Co. Ltd.), d-[8,9-3H] Biotin (product name, manufactured by GE Healthcare Bioscience Co. Ltd.), d-[carbonyl-14C] Biotin (product name, manufactured by GE Healthcare Bioscience Co. Ltd.), [1-14C] stearic acid (product name, manufactured by GE Healthcare Bioscience Co. Ltd.) and the like.

Examples of the silane-coupling agent having a substituent group include an amino group-containing silane-coupling agent, such as γ-aminopropyltriethoxysilane (APS), 3-[2-(2-aminoethylamino)ethylamino]propyltriethoxysilane, N-2-(aminoethyl)-3-aminopropylmethyldimethoxysilane or 3-aminopropyltrimethoxysilane. Among them, APS is preferable.

The silane compound to be polymerized is not particularly limited, and examples thereof include tetraethoxysilane (TEOS), γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyl-triethoxysilane. Among them, TEOS, MPS, and APS are preferable.

A group of spherical or almost spherical silica particles can be prepared by the method described above. Specifically, the almost spherical fine particle means a particle having a major axis/minor axis ratio of 2 or less.

For obtaining silica particles having a desired average diameter, it is preferable to perform filtration by using an ultrafiltration membrane such as YM-10 or YM-100 (trade names, manufactured by Millipore) for removal of particles having excessively larger and smaller particle diameters or to perform centrifugation at a suitable gravitational acceleration for recovery only of the supernatant or sediment.

Conventional nanoparticles such as latex particles are lower in dispersion stability, and copresence of a surfactant was needed for dispersion thereof in an aqueous solution such as buffer solution (see, for example, Masasumi Koishi and Takao Iwasaki, "Preparation of polymer particles," Ed., by Soc. Polymer Science, Japan, published by Kyoritsu Shuppan, 1994). When conventional nanoparticles such as latex particles are used as a labelling reagent such as the immunochromatographic reagent, it was known that the surfactant exerted an adverse effect as an impurity on the S/N ratio (Signal/Noise ratio).

On the other hand, the immunochromatographic labelled silica nanoparticles of the present invention is superior in dispersion stability in aqueous solutions such as buffer solution and can be dispersed without use of a surfactant. Therefore, there is no need to contain the surfactant for the dispersion. Thus, there is no adverse effect by the surfactant generated when the nanoparticles are used as an immunochromatographic reagent.

In the present invention, the labelled substance is immobilized in the labelled silica nanoparticles. The labelled substance is, for example, a functional substance such as a fluorescent substance, a light-absorbing substance, a radioactive substance. The fluorescent substance, the light-absorbing substance or the radioactive substance is not particularly limited, and, for example, an organic molecule, an inorganic compound, a semiconductor particle, or the like. When the labelled substance is a fluorescent substance, a light-absorbing substance or a radioactive substance, the concentration of the fluorescent substance, the light-absorbing substance or the radioactive substance in the labelled silica nanoparticles is preferably 20 mmol/l or more, more preferably 40 to 80 mmol/l.

Herein, the "concentration of the fluorescent substance, the light-absorbing substance or the radioactive substance in the labelled silica nanoparticles" is a value obtained by dividing the molar number of the fluorescent substance, the light-absorbing substance or the radioactive substance by the volume of the labelled silica nanoparticles. The molar number of the fluorescent substance or the light-absorbing substance is determined from the absorbance or fluorescence intensity of the labelled silica nanoparticles.

Further, the molar number of the radioactive substance was determined from the radiation quantity from the labelled silica nanoparticles.

Further, the volume of the labelled silica nanoparticles is obtained by separating the labelled silica nanoparticles from the labelled silica nanoparticles dispersion by centrifugation or ultrafiltration, drying and weighing the particles, and dividing the mass by the silica particle density of 2.3 g/cm$^3$.

For use of the labelled silica nanoparticles in immunochromatographic methods, the silica nanoparticles are preferably surface-modified with an analyte-recognizing substance (e.g., biological molecule such as antibody, antigen, DNA, or RNA) and the silica nanoparticles are more preferably surface-modified with antibody.

When the analyte-recognizing substance (the substance recognizing the analyte) is an antibody, the antibody binding amount on a surface area of 1 m$^2$ of the silica nanoparticle is preferably 0.35 mg to 7 mg, more preferably 0.7 mg to 3.5 mg.

The binding amount of the analyte-recognizing substance to the silica nanoparticles is determined by measuring the analyte-recognizing substance contained in the solution, which is obtained by removal of particles from the surface modification reaction solution by centrifugation or ultrafiltration, quantitatively by a common protein analysis method (e.g., BCA (bicinchoninic acid) method, UV method, Lowry method, or Bradford method) and also measuring the amount of the analyte-recognizing substance decreased.

In the present specification and claims, the analyte-containing sample solution is not particularly limited, and examples thereof include urine, blood and the like.

In the present specification and claims, the analytes to be detected, quantified, tested, diagnosed or judged include antigens, antibodies, DNAs, RNAs, saccharides, sugar chains, ligands, receptors, peptides, chemicals and the like. More specifically, an important pregnancy marker antigen, human gonadotropin (hCG)-peptide hormone in urine, is tested as an analyte for evaluation or diagnosis of pregnancy.

The method of binding the analyte-recognizing substance to the labelled silica nanoparticles is not particularly limited, and thus, the analyte-recognizing substance may be adsorbed on the labelled silica nanoparticles, for example, by electrostatic attractive force, Van der Waals force, hydrophobic interaction, or the like, or bonded thereto chemically by using a crosslinking or condensation agent. Yet alternatively, a thiol group may be introduced onto the surface of the labelled silica nanoparticles by using a thiol group-containing silane-coupling agent such as MPS (γ-mercaptopropyltriethoxysilane) and bound to the thiol group of the analyte-recognizing substance by forming a S—S bond.

If the particles aggregate when an analyte-recognizing substance, such as the biological molecule (e.g., antibody, antigen, DNA, or RNA) on the labelled silica nanoparticle surface described above, is bound thereto, the labelled silica nanoparticle surface may be previously surface-treated by alternating adsorption method. The alternating adsorption method is a method of forming a polymer thin film on the surface of a charged substrate or particles by allowing adsorption of a charged polymer thereon by electrostatic attractive force. It is possible to charge the particle surface by alternating adsorption on the surface of the labelled silica nanoparticles, which generates electrostatic repulsive force between particles and improves dispersibility. In addition, the polymer bound to the particles, which has an excluded volume, also improves dispersion by steric repulsion force.

Hereinafter, the immunochromatographic reagent of the present invention will be described.

The immunochromatographic reagent of the present invention comprises the labelled silica nanoparticles, and is preferably surface-modified with an analyte-recognizing substance, as described above, and is more preferably surface-modified with antibody.

The immunochromatographic reagent of the present invention is preferably silica nanoparticles containing a light-absorbing substance, a fluorescent substance or a radioactive substance as the labelled substance as described above.

The light-absorbing substance is not particularly limited, if it is a substance absorbing light from any light source described above, but, for detection with a commonly-used detector such as plate reader (e.g., Vmax (trade name: manufactured by Molecular Devices), micro plate reader MPR-A4i (trade name: manufactured by Toso Corporation)) and from the viewpoint of data compatibility, a light-absorbing substance having a maximum absorption wavelength of absorption spectrum in the range of 200 to 800 nm is preferable, and a light-absorbing substance having a maximum absorption wavelength of absorption spectrum in the range of 400 to 700 nm is more preferable.

The "maximum absorption wavelength" herein is the wavelength of the peak having the strongest absorption among the absorption peaks when there are multiple absorption peaks present in the absorption spectrum.

Any light-absorbing dye may be used, if it has a maximum absorption wavelength of absorption spectrum in the range of 200 to 800 nm, but, for example, an NHS ester of DYQ-660 (trade name, manufactured by Dyomics GmbH) represented by the following Formula is preferable.

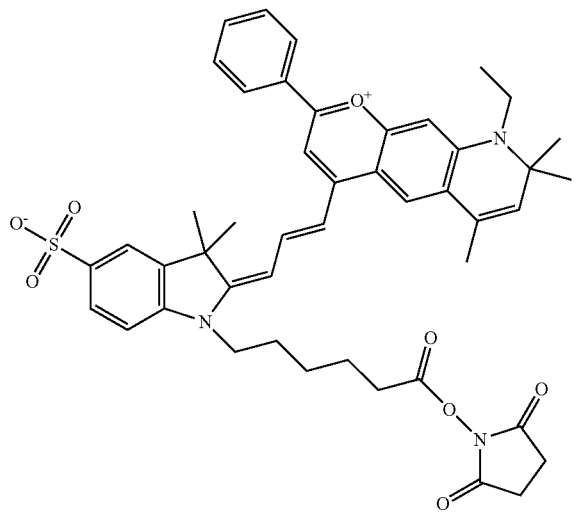

DYQ-660-NHS

The silica nanoparticles containing the light-absorbing substance has a molar extinction coefficient ε of $5 \times 10^7$ $M^{-1}$ $cm^{-1}$ or more, and ε is preferably $2 \times 10^8$ $M^{-1}$ $cm^{-1}$ to $1 \times 10^{11}$ $M^{-1}$ $cm^{-1}$.

The absorbance, absorption spectrum and ε of the silica nanoparticles containing a light-absorbing substance may be determined by using any absorptiometer or plate reader, as the silica nanoparticles are dispersed, for example, as aqueous dispersion, ethanol dispersion, or N,N-dimethylformamide dispersion.

The "molar extinction coefficient ε of the silica nanoparticles containing a light-absorbing substance" is a molar extinction coefficient ε of the silica nanoparticles containing a light-absorbing substance in dispersion, as determined by measuring the absorbance of the dispersion of the silica nanoparticles containing a light-absorbing substance and calculating according to the Lambert-Beer's equation.

In the immunochromatographic reagent of the present invention, when used are silica nanoparticles obtained by surface-modification of the silica nanoparticles containing a fluorescent substance as the labelled substance with an analyte-recognizing substance, it is possible to achieve high-sensitivity detection or quantitative determination, by detecting the fluorescence emitted from the silica nanoparticles.

The fluorescent substance is not particularly limited, but for detection with a commonly-used detector (e.g., AE-6931FXCF Printgraph (trade name, manufactured by ATTO)) and from the viewpoint of data compatibility, a fluorescent substance emitting blue fluorescence (440 to 490 nm), yellow fluorescence (540 to 590 nm), orange fluorescence (590 to 620 nm) or red fluorescence (620 to 740 nm) is preferable.

Hereinafter, the immunochromatographic test strip of the present invention will be described.

The immunochromatographic test strip of the present invention has (1) a sample application member (sample pad) and a member impregnated with the labelled silica particles (conjugate pad), and (2) the conjugate pad and a membrane having an antibody-immobilized region (antibody-immobilized membrane), and (3) that are connected to each other in series, so that there is capillary phenomenon generated between the antibody-immobilized membrane and the absorption pad.

A preferable embodiment of the immunochromatographic test strip of the present invention will be described with reference to FIGS. 1a and 1b.

Figure 1B:
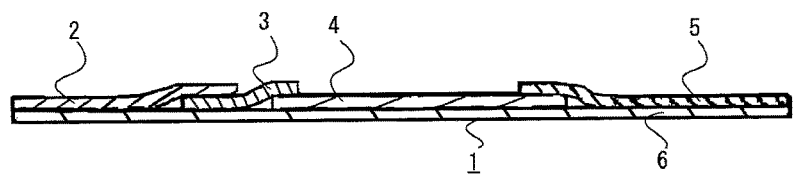

FIG. 1a is a top view illustrating the immunochromatographic test strip of the present invention, and FIG. 1b is a cross-sectional view of the immunochromatographic test strip in the top view.

The immunochromatographic test strip 1 of the present invention preferably has a sample application member (sample pad) 2, a labelled silica nanoparticle-impregnated member (conjugate pad) 3, an antibody-immobilized membrane 4, and an absorption pad 5. Each constituent member is more preferably supported by a backing sheet 6 with adhesive.

The antibody-immobilized region of the membrane 4 preferably has a test line 41 where a capturing antibody for evaluation of presence or absence of an analyte, i.e., for judgment of positivity or negativity, is immobilized and a control line 42 where antibodies for capturing all analytes labelled by the labelled silica particles are immobilized.

Hereinafter, each of the members above will be described.
1) Sample Application Member (Sample Pad) 2

The sample pad 2 is a constituent member where an analyte-containing sample is applied dropwise.
2) Labelled Silica Nanoparticle-impregnated Member (Conjugate Pad) 3

The conjugate pad 3 is a constituent member impregnated with the labelled silica nanoparticles, where the analyte contained in the sample solution moving from the sample pad 2 by capillary phenomenon is captured and labelled by the labelled silica particles by molecular recognition reaction such as antigen-antibody reaction.

The content of the labelled silica nanoparticles per unit area ($cm^2$) of the conjugate pad 3 is not particularly limited, but preferably 50 µg to 2 mg. The impregnation may be effected, for example, by coating, dropwise application, or spraying of the dispersion of the labelled silica particles and subsequent drying.
3) Antibody-immobilized Membrane 4

The membrane 4 is a constituent member where the analyte labelled by the silica nanoparticles moves by capillary phenomenon and which has an antibody-immobilized region (judgment region) carrying out a reaction forming a sandwiched immunocomplex in the form of immobilized antibody-analyte-labelled silica nanoparticle.

The shape of the antibody-immobilized region (judgment region) in the membrane is not particularly limited, if the capturing antibody is immobilized locally there, and may be linear, circular, belt-shaped and the like in shape, but preferably linear, more preferably linear with a width of 0.5 to 1.5 mm.

The analyte labelled with silica particles can be captured in the antibody-immobilized region (judgment region) by the reaction forming an sandwiched immunocomplex in the form of immobilized antibody-analyte-labelled silica nanoparticles, and it is possible to determine presence or absence of the analyte, i.e., to determine positivity or negativity, by the degree of the coloring or fluorescence derived from the silica nanoparticles on the complex formed. Thus, the labelled silica particles are concentrated in the antibody-immobilized region (judgment region), allowing detection and judgment visually as coloring signal or by analysis with a detecting device.

For sufficient completion of the sandwiched immunocomplex-forming reaction or for prevention of the influence on measurement by the coloring substance in the liquid sample and by the labelled silica nanoparticles not bound to the analyte, the judgment region in the membrane is preferably formed as it is separated from the end connected to the conjugate pad and also from the end connected to the absorption pad to some extent (e.g., located in the middle of the membrane).

The amount of the antibody immobilized in the antibody-immobilized region (judgment region) is not particularly limited, but when the shape of the antibody-immobilized region is linear, it is preferably 0.5 µg to 5 µg per unit length (cm). The immobilization may be performed, for example, a method of physical adsorption by coating, dropwise application or spraying of the antibody solution and subsequent drying.

For prevention of the influence on measurement by non-specific adsorption after the antibody immobilization described above, the membrane is preferably subjected to so-called blocking treatment entirely. For example, the membrane is immersed in a buffer solution containing a blocking agent such as albumin, casein or polyvinylalcohol for a suitable period and then dried. Examples of the commercially available blocking agents include Skimmilk (manufactured by DIFCO), 4% Block Ace (manufactured by Meiji Dairies Corp.) and the like.
4) Absorption Pad 5

The absorption pad 5 is a constituent member generating a particular flow by absorbing the sample solution and the labelled silica particles moving through the membrane by capillary phenomenon.

The material for each constituent member is not particularly limited, and any material used for immunochromatographic test strip may be used, but a glass fiber pad such as Glass Fiber Conjugate Pad (trade name: manufactured by MILLIPORE) is preferable as the sample pad and the conjugate pad; a nitrocellulose membrane such as Hi-Flow Plus120 membrane (trade name: manufactured by MILLIPORE) is preferable as the membrane; and a cellulose membrane such as Cellulose Fiber Sample Pad (trade name: manufactured by MILLIPORE) is preferable as the absorption pad.

The backing sheet with adhesive is, for examples, AR9020 (trade name, manufactured by Adhesives Research).

The test strip may be prepared by placing a sample application member (sample pad), a labelled silica particle-impregnated member (conjugate pad), an antibody-immobilized membrane, and an absorption pad in that order (preferably on a backing sheet), while bonding one end of each unit onto the end of the next member with an overlapping a width of approximately 1 to 5 mm to cause capillary phenomenon between respective members.

Needless to say, the degree of color development can be determined by visual observation and also by using a tester for urine test paper such as Pretester RM-405 or Pretester RM-505 (trade names, manufactured by Wako Pure Chemical Industries, Ltd.), a densitometer, or the like.

The test strip is preferably placed in a housing (casing), for example, of a plastic material with an observation window for visual examination of the detection line of test strip, for easier operation by general users who are not skilled in operation and from the point of POCT. For example, the housing described in JP-A-2000-356638 ("JP-A" means unexamined published Japanese patent application) and the like are used favorably.

The labelled silica nanoparticles as the immunochromatographic reagent of the present invention can emit lights in various hues (colors) and at various fluorescence wavelengths, by containing different kinds of labelled substances. By using two or more of the labelled silica nanoparticles thus obtained it is possible, for example, to detect, quantify, judge or diagnose two or more analytes simultaneously in one operation on the test strip.

Then, the two or more labelled silica nanoparticles should be surface-modified respectively with substances recognizing different analytes molecularly.

Specific examples thereof include an immunochromatographic reagent comprising red dye (e.g., rhodamine)-containing silica nanoparticles surface-modified with a mouse anti-influenza A virus nucleoprotein monoclonal antibody that recognizes influenza A virus nucleoprotein and blue dye (e.g., DYQ-660 (trade name, manufactured by Dyomics))-containing silica nanoparticles surface-modified with a mouse anti-influenza B virus nucleoprotein monoclonal antibody that recognizes influenza B virus nucleoprotein, and a test strip by using the same.

With the immunochromatographic reagent containing two or more labelled silica nanoparticles described above and the test strip by using the same, it is possible to detect, quantify, judge or diagnose two or more analytes simultaneously based on the difference in hue of color formation or in fluorescence wavelength in the same antibody-immobilized region. The same antibody-immobilized region is preferably linear in shape.

The color (hue) and the emission wavelength of conventional nanoparticles (e.g., gold nanoparticle), which often emits a single-colored light or a fluorescence at a single wavelength, were very restricted. Therefore, when such conventional nanoparticles are used in the immunochromatographic method, it was substantially difficult to detect or judge two or more analytes, and thus, needed to form antibody-immobilized regions (judgment regions) carrying different immobilized antibodies on a membrane at different positions. When multiple antibody-immobilized regions are formed at positions close to each other, the color formation or emission signal from analytes often cause confusion, because the regions emit a light in a single colors or a fluorescent light at a single wavelength.

In contrast, the labelled silica nanoparticles can be provided by containing different kinds of labelled substance with various hues, various fluorescence wavelengths and the like, and thus, it is possible to detect, quantify, judge or diagnose multiple kinds of analytes simultaneously, as multiple kinds of antibodies are immobilized in a single antibody-immobilized region in the test strip of the present invention.

Specifically, for example, when analytes A and B are to be measured, an immobilized test strip having an a single antibody-immobilized region carrying immobilized antibodies to the analytes A and B is prepared by using blue dye (e.g., DYQ-660 (trade name, manufactured by Dyomics))-containing silica nanoparticles surface-modified with an analyte A-recognizing antibody or the fragment thereof and yellow dye (e.g., fluorescein)-containing silica nanoparticles surface-modified with an analyte B-recognizing antibody or the fragment thereof. It is possible to decide whether the analytes are present, by applying an unknown sample solution possibly containing the analytes A and B dropwise on the sample pad of the test strip and observing the antibody-immobilized region. In the specific example above, blue hue (color) of the reaction line indicates major presence of the substance A, while yellow color, of the substance B, and when the analytes A and B are present in almost the same amounts, a reaction line green in color is observed. In this way, it is possible to determine the abundance ratio of the analytes by detecting the color by visual observation or by using a detecting device qualitatively or quantitatively, by using the fact that the hue (color) of the reaction line observed changes according to the abundance ratio of the substances A and B.

It is possible to analyze an analyte semi-quantitatively, by assuming negative when the color tone is thinner than a particular color and positive when it is thicker. Needless to say, the degree of color development may be determined, for example, by using a tester for urine test paper such as Pretester RM-405, Pretester RM-505 (trade names, manufactured by Wako Pure Chemical Industries, Ltd.), a densitometer, or the like.

Qualitative analysis is normally performed in advance to quantitative analysis, and the "semi-quantitative determination" herein above is a qualitative analysis slightly more quantitative numerically that is performed before qualitative analysis.

Hereinafter, the immunochromatographic fluorescence-detecting system or the radiation-detecting system of the present invention will be described.

When silica nanoparticles containing a fluorescent substance as the labelled substance are used as an immunochromatographic reagent, the immunochromatographic fluorescence-detecting system of the present invention can be used similarly to the test strip described above.

In other words, the fluorescence-detecting system of the present invention has at least following components (1) and (2):

(1) a test strip comprising a sample pad, a member impregnated with fluorescent substance-containing silica nanoparticles (conjugate pad), an antibody-immobilized membrane and an absorption pad, and (2) an excitation light source.

The test strip is preferably supported by a backing sheet.

In the fluorescence-detecting system of the present invention, the excitation light source preferably emits an excitation light at a wavelength of 200 nm to 400 nm, for detection of the fluorescence from the silica nanoparticles, for example, by visual observation. Examples of the excitation light sources include mercury lamp, halogen lamp, and xenon lamp.

In addition, the fluorescence-detecting system of the present invention more preferably has a filter for transmission of a light at a particular wavelength from the excitation light source, and furthermore preferably has a filter transmitting only fluorescent light while blocking the excitation light for detection only of fluorescence for example by visual observation.

The fluorescence-detecting system of the present invention particularly preferably has a photoelectron multiplier or CCD detector for detection of the fluorescence, and it is possible in this way to detect a fluorescence at an intensity or wavelength that is not detected by visual observation. In addition, it is possible to perform high-sensitivity detection and quantitative determination of an analyte, because the fluorescence intensity can be measured.

When silica nanoparticles containing a radioactive substance as the labelled substance are used as an immunochromatographic reagent, the immunochromatographic radiation-detecting system of the present invention can be used similarly to the test strip described above.

In other words, the radiation-detecting system of the present invention has at least following components (1) and (2):

(1) a test strip comprising a sample pad, a member impregnated with radioactive substance-containing silica nanoparticles (conjugate pad), an antibody-immobilized membrane and an absorption pad, and (2) a Geiger counter or an X-ray film.

In the immunochromatographic radiation-detecting system of the present invention, it is possible to perform detection and quantitative determination of an analyte, by measuring radiation (radioactive ray) from the silica nanoparticles by means of a Geiger counter or by photosensitizing radiation from the silica nanoparticles to an X-ray film The labelled silica nanoparticles for immunochromatographic reagent of the present invention can provide various light absorption characteristics, fluorescence characteristics or the like by varying a labelled substance contained therein, so that the labelled silica nanoparticles for immunochromatographic reagent of the present invention can be used favorably in various immunochromatographic methods.

Further, the labelled silica nanoparticles for immunochromatographic reagent of the present invention do not offer blacken color, even if the labelled silica nanoparticles aggregate or the like.

The immunochromatographic reagent of the present invention, which employs the labelled silica nanoparticles surface-modified with an analyte-recognizing substance and thus provides various light absorption characteristics, fluorescence characteristics or the like, can be suitably used in simultaneous analysis of multiple analytes.

The immunochromatographic test strip of the present invention, which employs the immunochromatographic reagent, can be used in simultaneous detection and quantitative determination or judgment of multiple analytes and thus, suitable as a new POCT diagnostic method.

Further, the immunochromatographic fluorescence-detecting system of the present invention, which employs silica nanoparticles containing a fluorescent substance as the immunochromatographic reagent, allows high-sensitivity detection or quantitative determination by detection of fluorescence.

Further, the immunochromatographic radiation-detecting system of the present invention, which employs silica nanoparticles containing a radioactive substance as the immunochromatographic reagent, allows high-sensitivity detection or quantitative determination by detection of radiation.

EXAMPLES

The present invention will be described in more detail based on the following examples, but the invention is not intended to be limited thereto.

Reference Example 1 (Preparation of Labelled Silica Nanoparticles for Use in the Present Invention 2.9 mg of 5- (and -6)-carboxytetramethylrhodamine succinimidyl ester (trade name, manufactured by emp Biotech GmbH) was dissolved in 1 ml of dimethylformamide (DMF). 1.3 µl of APS was added thereto, and the mixture was allowed to react at room temperature (23° C.) for 1 hour. 128 ml of ethanol, 400 µl of TEOS, 28.8 ml of distilled water, and 400 µl of 28 mass % aqueous ammonia were added to 400 µl of the reaction solution obtained, and the mixture was allowed to react at room temperature for 24 hours.

The reaction solution was centrifuged at a gravitational acceleration of 18000×g for 30 minutes, and the supernatant was removed. The precipitated silica particles were redispersed in 4 ml of distilled water, and the dispersion was centrifuged again at a gravitational acceleration of 18000×g for 30 minutes. The above washing operation was repeated twice additionally, the unreacted TEOS and ammonia contained in the labelled silica nanoparticles dispersion were removed, to give 100.8 mg of silica nanoparticles having an average diameter of 104 nm (yield: approximately 94%).

Figure 2:
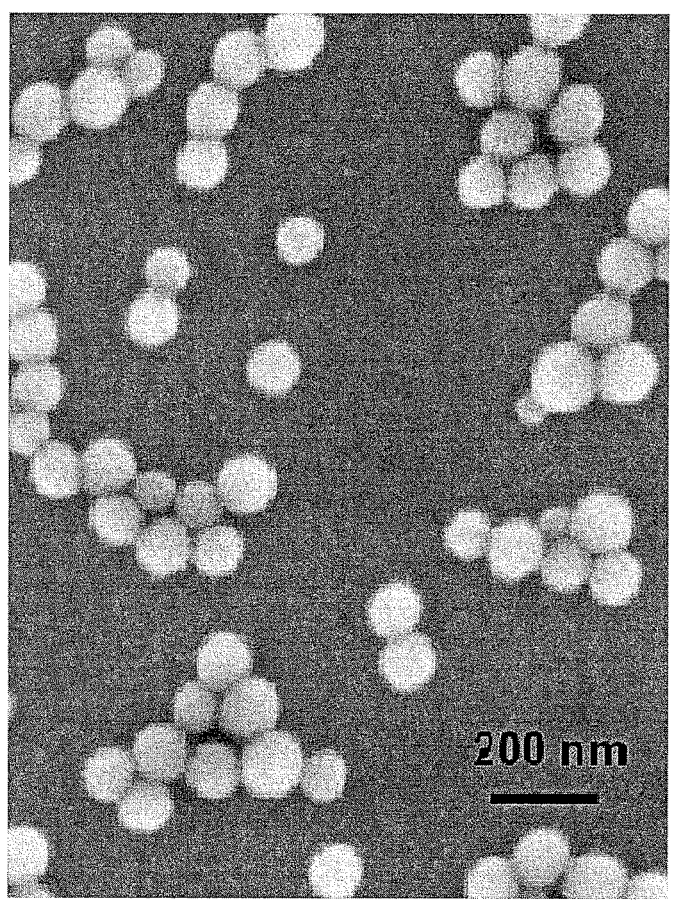
FIG. 2 is a TEM micrograph showing the labelled substance-containing silica nanoparticles obtained.

FIG. 2 is a SEM micrograph showing the labelled silica nanoparticles obtained. In the Figure, white spherical substances are the labelled silica nanoparticles obtained.

Example 1 (Detection of hCG)

1 mL of 50 mM $KH_2PO_4$ (pH 7.5) and 8 mL of the rhodamine-containing silica nanoparticle dispersion (6.25 mg/mL) were placed and agitated gently in a centrifuge tube. 1 mL (5 mg/mL) of an anti-hCG antibody (Anti-hCG clone codes/5008, manufactured by Medix Biochemica) was added into the centrifuge tube while the mixture was agitated, and the mixture was agitated at room temperature for 1 hour, allowing the anti-hCG antibody to be adsorbed on the silica nanoparticles. 100 µL of the reaction solution was placed in a microtube, and designated as colloid A. Residual of the reaction solution was designated as colloid B.

The colloid A was centrifuged at 12000×g for 15 minutes, and the supernatant was collected. The concentration of the anti-hCG antibody contained in the supernatant, as determined by the BCA method, was 239 µg/ml. Because the concentration of the anti-hCG antibody at the start of reaction was 500 µg/ml and the weight concentration of the silica nanoparticle was 5 mg/mL, 52.2 mg of anti-hCG antibody was bound to 1 g of the silica nanoparticles. The surface area of 1 g of the silica nanoparticles, as calculated assuming that the density of the silica nanoparticles is 2.3 g/cm$^3$ and the particle diameter of the silica nanoparticles 104 nm, is 25.1 m$^2$. Accordingly, the amount of the anti-hCG antibody bound to the silica nanoparticles per 1 m$^2$ of surface area was determined to be 2.1 mg.

0.55 mL of 1% PEG (polyethylene glycol, molecular weight: 20,000, manufactured by Wako Pure Chemical Industries, Ltd.) was added thereto; the mixture was agitated gently; 1.1 mL of 10% BSA was added additionally; and the mixture was agitated gently.

The mixed liquid was centrifuged at 12000×g for 15 minutes; the supernatant was removed as about 1 mL thereof was left behind; and the sediment was dispersed in the remaining supernatant. 20 mL of storage buffer (20 mM Tris-HCl (pH 8.2), 0.05% PEG 20,000, 150 mM NaCl, 1% BSA, 0.1% $NaN_3$) was added to the dispersion, and the mixture was centrifuged again; the supernatant was removed, as about 1 mL of it was left behind; and the sediment was redispersed in the remaining supernatant. 1 mL of distilled water and 2 mL of a coating buffer (20 mM Tris-HCl (pH 8.2), 0.05% PEG (molecular weight: 20,000), 150 mM NaCl, 1% BSA, 0.1% $NaN_3$) were added to the dispersion, and the mixture was agitated gently.

The dispersion of the silica nanoparticle carrying the adsorbed antibody thus obtained was applied uniformly on a sheet of Glass Fiber Conjugate Pad (GFCP, manufactured by MILLIPORE) (8×150 mm) in an amount of 0.8 mL. The sheet was dried in desiccator at room temperature overnight under reduced pressure, to give a conjugate pad containing the silica nanoparticles obtained in Reference Example 1.

An antibody-immobilized membrane was prepared by applying a solution ((50 mM KH$_2$ PO$_4$, pH 7.0)+5% sucrose) containing 1 mg/mL of an anti-hCG antibody (α subunit of FSH (LH), clone code/6601, manufactured by Medix Biochemica) in a coating amount of 0.75 μL/cm, as a test line having a width of approximately 1 mm in the central region of a membrane (Length: 25 mm, product name: Hi-Flow Plus120 membrane, manufactured by MILLIPORE) (separated by approximately 12 mm from the edge).

Subsequently, a solution ((50 mMKH$_2$ PO$_4$, pH 7.0) sugar-free) containing 1 mg/mL of an anti-IgG antibody (Anti Mouse IgG, manufactured by Dako) was coated thereon as a control line having a width of approximately 1 mm in a coating amount of 0.75 μL/cm and the resulting membrane was dried at 50° C. for 30 minutes.

Then, the membrane was immersed in a blocking buffer at room temperature for 30 minutes for blocking processing. It was transferred into a membrane washing/stabilizing buffer and left still at room temperature for 30 minutes or more. The membrane was withdrawn, placed on a paper towel, and dried at room temperature overnight, to give an antibody-immobilized membrane.

The membrane obtained above, the conjugate pad obtained above, a sample pad (Glass Fiber Conjugate Pad (GFCP), manufactured by MILLIPORE), and an absorption pad (Cellulose Fiber Sample Pad (CFSP), manufactured by MILLIPORE) were placed on a backing sheet (product name: AR9020, manufactured by Adhesives Research), and the composite was cut into strips having a width of 5 mm and a length of 60 mm, to give test strips in the configuration shown in FIGS. 1a and 1b. The FIGS. 1a and 1b are described above.

As shown in FIGS. 1a and 1b, respective constituent members were placed overlapped with the neighboring members at both ends to a width of about 2 mm (hereinafter, the same shall apply).

When 50 IU/L of a recombinant hCG (manufactured by ROHTO Pharmaceutical Co., Ltd.) was applied dropwise onto the sample pad region of the strip in an amount of 100 μL and the strip was left for one minute, it was confirmed that the line containing the coated anti-hCG antibody (α subunit of FSH (LH), clone code/6601, manufactured by Medix Biochemica) (test line) and the line containing the coated anti-IgG antibody (control line) developed red color.

Example 2 (Detection of Multiple Biological Molecules with the Same Line)

Rhodamine-containing silica nanoparticles were prepared in a similar manner to Reference Example 1 (average diameter: 101 nm, yield: 90%). Separately, DYQ-660-containing silica nanoparticles were prepared in a manner similar to Reference Example 1 by using DYQ-660-NHS-Ester (manufactured by Dyomics GmbH). Subsequently in a similar manner to Example 1, the rhodamine-containing silica nanoparticles were surface-modified with a mouse anti-influenza A virus nucleoprotein monoclonal antibody by adsorption, and the DYQ-660-containing silica nanoparticles were surface-modified with a mouse anti-influenza B virus nucleoprotein monoclonal antibody by adsorption.

0.8 mL of the dispersion containing the rhodamine-containing silica nanoparticles surface-modified with mouse anti-influenza A virus nucleoprotein monoclonal antibody by adsorption was applied uniformly on a conjugate pad (Glass Fiber Conjugate Pad (GFCP), 8×150 mm, manufactured by MILLIPORE), and the pad was dried in desiccator overnight under reduced pressure. Subsequently, 0.8 mL of a dispersion containing the DYQ-660-containing silica nanoparticles surface-modified with mouse anti-influenza B virus nucleoprotein monoclonal antibody was applied uniformly on the same conjugate pad, and the pad was dried in desiccator overnight under reduced pressure. In this way, a conjugate pad impregnated both with rhodamine-containing silica nanoparticles and DYQ-660-containing silica nanoparticle was prepared.

Subsequently, an antibody-immobilized membrane was prepared by applying a solution containing a mouse anti-influenza A virus nucleoprotein monoclonal antibody and a mouse anti-influenza B virus nucleoprotein monoclonal antibody respectively at 1 mg/mL, on the central region of a membrane (Length: 25 mm, product name: Hi-Flow Plus120 membrane, manufactured by MILLIPORE) (separated by approximately 12 mm from edge) as a test line having a width of approximately 1 mm in a coating amount of 0.75 μL/cm, and the resulting membrane was dried at 50° C. for 30 minutes. Further, an anti-mouse antibody rabbit polyclonal antibody (1 mg/mL) was coated in a coating amount of 0.75 μL/cm as the control line, and the membrane was dried at 50° C. for 30 minutes.

The membrane obtained above, the conjugate pad obtained above, a sample pad (Glass Fiber Conjugate Pad (GFCP), manufactured by MILLIPORE), and an absorption pad (Cellulose Fiber Sample Pad (CFSP), manufactured by MILLIPORE) were placed on a backing sheet (product name: AR9020, manufactured by Adhesives Research); the composite was cut into strips having a width of 5 mm and a length of 60 mm, to give test strips in the configuration shown in FIGS. 1a and 1b. The FIGS. 1a and 1b are described above.

Two of the test strips were made available, a solution containing influenza A virus at $5 \times 10^2$ FFU/mL was applied dropwise on one of them, and the strip was left still for one minute. A solution containing influenza B virus at $5 \times 10^2$ FFU/mL was applied dropwise on the other test strip, and the strip was left still for one minute. The line on the test strip where the influenza A virus-containing solution was applied dropwise turned red, while the sample line of the test strip where the influenza B virus-containing solution was applied dropwise turned blue.

Example 3 (High-sensitivity Detection of Fluorescence)

Fluorescein-containing silica particles were prepared in a similar manner to Reference Example 1 (average diameter: 93 nm, yield: 88%) and surface-modified with an anti-hCG antibody (Anti-hCG clone codes/5008, manufactured by Medix Biochemica) by adsorption in a similar manner to Example 1. In a similar manner to Example 1, 0.8 ml of the fluorescein-containing silica nanoparticles surface-modified with the anti-hCG antibody by adsorption was coated on a Glass Fiber Conjugate Pad (GFCP, 8×150 mm, manufactured by MILLIPORE), which was dried in desiccator overnight under reduced pressure. In this way, a conjugate pad containing fluorescein-containing silica nanoparticles was prepared.

In a similar manner to Example 1, a membrane (Hi-Flow Plus120 membrane, manufactured by MILLIPORE) carrying an anti-hCG antibody (α subunit of FSH (LH), clone code/6601, manufactured by Medix Biochemica) as the test line and an anti-IgG antibody (Anti Mouse IgG, manufactured by Dako) as the control line, a conjugate pad, an absorption pad (CFSP, manufactured by MILLIPORE), and a sample pad (GFCP, manufactured by MILLIPORE) were placed on a backing sheet (product name: AR9020, manufactured by Adhesives Research); the composite was cut into strips having a width of 5 mm and a length of 60 mm, to give test strips in the configuration shown in FIGS. 1a and 1b. The FIGS. 1a and 1b are described above.

100 µL of 0.5 IU/L recombinant hCG (manufactured by ROHTO Pharmaceutical Co., Ltd.) was applied dropwise on the sample pad of the test strip, and the pad was left still for one minute.

The test strip was irradiated by a mercury lamp (103W), while a filter FF01-482 (trade name, manufactured by Semrock, Inc.) was used as the filter in the excitation light source side and a filter FF01-536 (trade name, manufactured by Semrock, Inc.) as the filter in the detector side, and the imaging was performed by using a CCD detector (C2741-35 A (trade name, manufactured by Hamamatsu Photonics K.K.)) as the detector. As a result, there was confirmed fluorescent emission from the test and control lines.

The results show that the test strip in Example 3 allows detection of analyte (combinant hCG) in an amount of $\frac{1}{100}$ of that observable by visual observation in Example 1 indicating that it is possible to perform high-sensitivity detection with fluorescence.

Having described our invention as related to the present embodiments, it is our intention that the invention not be limited by any of the details of the description, unless otherwise specified, but rather be construed broadly within its spirit and scope as set out in the accompanying claims.

What is claimed is:

1. An immunochromatographic test strip, comprising
a sample application member,
a member impregnated with an immunochromatographic reagent comprising labelled silica nanoparticles which are both surface-modified with at least one analyte-recognizing substance and bonded with polyethylene glycol and bovine serum albumin (BSA), wherein the labelled silica nanoparticles have an active group that-forms a covalent bond to a silane-coupling agent, wherein the active group is selected from the group consisting of a N-hydroxysuccinimide (NHS) ester group, a maleimide group, an isocyanate group, an isothiocyanate group, an aldehyde group, a para-nitrophenyl group, a diethoxymethyl group, an epoxy group, or a cyano group,
wherein the silane-coupling agent comprises 3-[2-(2-aminoethylamino)ethylamino]propyltriethoxysilane,
a membrane having an antibody-immobilized region in which the labelled silica nanoparticles are captured by a sandwiched immunocomplex-forming reaction to form immobilized antibody-analyte-labelled silica nanoparticles, and
an absorption pad that are connected in series.

2. The immunochromatographic test strip according to claim 1, wherein two or more kinds of analytes are detected simultaneously, based on the difference in hue of color formation or fluorescence wavelength in a single antibody-immobilized region, with the immunochromatographic reagent, wherein two or more labelled silica nanoparticles are surface-modified with two or more analyte-recognizing substances, and wherein each labelled silica nanoparticle is surface-modified by a different analyte-recognizing substance.

3. The immunochromatographic test strip according to claim 1, wherein the silane-coupling agent further comprises N-2-(aminoethyl)-3-aminopropylmethyldimethoxysilane and/or 3-aminopropyltrimethoxysilane.

4. An immunochromatographic fluorescence-detecting system, comprising:
an immunochromatographic test strip, comprising
1) a sample application member,
2) a member impregnated with an immunochromatographic reagent comprising labeled silica nanoparticles, wherein said labelled silica nanoparticles are both surface-modified with at least one analyte-recognizing substance and bonded with polyethylene glycol and bovine serum albumin (BSA), wherein the labelled silica nanoparticles have an active group that forms a covalent bond to a silane-coupling agent, wherein the active group is selected from the group consisting of a N-hydroxysuccinimide (NHS) ester group, a maleimide group, an isocyanate group, an isothiocyanate group, an aldehyde group, a para-nitrophenyl group, a diethoxymethyl group, an epoxy group, or a cyano group, and
wherein the silane-coupling agent comprises 3-[2-(2-aminoethylamino)ethylamino]propyltriethoxysilane,
3) a membrane having an antibody-immobilized region in which the labelled silica nanoparticles are captured by a sandwiched immunocomplex-forming reaction to form immobilized antibody-analyte-labelled silica nanoparticles, and
4) an absorption pad,
wherein 1)-4) are connected in series, and
wherein the immunochromatographic reagent allows high-sensitivity detection by detection of fluorescence emitted from the silica nanoparticles containing a fluorescent substance, and wherein the wavelength of an excitation light source used for detection of the fluorescence emitted from the silica nanoparticles is 200 nm to 600 nm.

5. The immunochromatographic fluorescence-detecting system according to claim 4, further comprising
a filter eliminating the excitation light and transmitting only the fluorescence.

6. The immunochromatographic fluorescence-detecting system according to claim 5, further comprising
a photoelectron multiplier or a CCD detector detecting the fluorescence,
wherein the system allows quantitative determination of the analyte by detection of the fluorescence and measurement of the fluorescent intensity with the photoelectron multiplier or the CCD detector.

7. The immunochromatographic fluorescence-detecting system according to claim 4, wherein the excitation light source is a mercury lamp, a halogen lamp, or a xenon lamp.

8. The immunochromatographic fluorescence-detecting system according to claim 4, wherein the silane-coupling agent further comprises N-2-(aminoethyl)-3-aminopropylmethyldimethoxysilane and/or 3-aminopropyltrimethoxysilane.

9. An immunochromatographic radiation-detecting system, comprising:
an immunochromatographic test strip, comprising
1) a sample application member,
2) a member impregnated with an immunochromatographic reagent comprising labelled silica nanoparticles containing a radioactive substance, wherein said labelled silica nanoparticles containing a radioactive substance are both surface-modified with at least one analyte-recognizing substance and bonded with polyethylene glycol and bovine serum albumin (BSA), wherein the labelled silica nanoparticles have an active group that forms a covalent bond to a silane-coupling agent, wherein the active group is selected from the group consisting of a N-hydroxysuccinimide (NHS) ester group, a maleimide group, an isocyanate group, an isothiocyanate group, an aldehyde group, a para-nitrophenyl group, a diethoxymethyl group, an epoxy group, or a cyano group, and wherein the silane-coupling agent comprises 3-[2-(2-aminoethylamino)ethylamino]propyltriethoxysilane, 3) a membrane having an antibody-immobilized region in which the labelled silica nanoparticles containing a radioactive substance are captured by a sandwiched-immunocomplex-forming reaction to form immobilized antibody-analyte-labelled silica nanoparticles containing a radioactive substance, and 4) an absorption pad, wherein 1)-4) are connected in series, and wherein radiation emitted from the labelled silica nanoparticles containing a radioactive substance is measured with a Geiger counter or by photosensitizing an X-ray film.

10. The immunochromatographic radiation-detecting system according to claim 9, wherein the silane-coupling agent further comprises N-2-(aminoethyl)-3-aminopropylmethyl-dimethoxysilane and/or 3-aminopropyltrimethoxysilane.

* * * * *